United States Patent [19]

Chandraratna et al.

[11] Patent Number: 5,618,836
[45] Date of Patent: Apr. 8, 1997

[54] [4-(1,2-EPOXYCYCLOHEXANYL)BUT-3-EN-1-YNYL]AROMATIC AND HETEROAROMATIC ACIDS AND DERIVATIVES HAVING RETINOID-LIKE BIOLOGICAL ACTIVITY

[75] Inventors: Roshantha A. Chandraratna, Missio Viejo; Richard L. Beard, Santa Ana Heights, both of Calif.

[73] Assignee: Allergan, Waco, Tex.

[21] Appl. No.: 419,626

[22] Filed: Apr. 10, 1995

Related U.S. Application Data

[62] Division of Ser. No. 177,620, Dec. 30, 1993, Pat. No. 5,426,118.

[51] Int. Cl.⁶ ........................... A61K 31/38; A61K 31/34
[52] U.S. Cl. .................. 514/444; 514/461; 514/475; 549/60; 549/472; 549/554
[58] Field of Search .................... 514/444, 461, 514/475; 549/60, 472, 554

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 548/237 |
| 4,391,731 | 7/1983 | Boller et al. | 252/299.62 |
| 4,695,649 | 9/1987 | Magami et al. | 560/86 |
| 4,723,028 | 2/1988 | Shude | 560/8 |
| 4,739,098 | 4/1988 | Chandraratna | 560/8 |
| 4,740,519 | 4/1988 | Shroot et al. | 514/519 |
| 4,810,824 | 3/1989 | Chandraratna | 514/311 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 514/432 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | . |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |

(List continued on next page.)

FOREIGN PATENT DOCUMENTS

| | | |
|---|---|---|
| 0098591 | 1/1984 | European Pat. Off. ...... C07D 333/54 |
| 0130795 | 1/1985 | European Pat. Off. ...... C07D 311/58 |
| 170105A | 5/1985 | European Pat. Off. . |
| 0176033 | 4/1986 | European Pat. Off. ...... C07D 261/18 |
| 0176032 | 4/1986 | European Pat. Off. ........ C07C 65/38 |
| 176034A | 4/1986 | European Pat. Off. ........ C07C 63/66 |
| 0253302 | 1/1988 | European Pat. Off. ...... C07D 213/16 |
| 0265069 | 4/1988 | European Pat. Off. ...... C07C 175/00 |
| 0272921 | 6/1988 | European Pat. Off. ...... C07D 213/80 |
| 0284288 | 9/1988 | European Pat. Off. ...... C07D 401/04 |
| 0303915 | 2/1989 | European Pat. Off. ..... A61K 31/255 |
| 0315071 | 5/1989 | European Pat. Off. ........ C07C 63/66 |
| 0350846 | 7/1989 | European Pat. Off. ...... C07D 311/58 |

(List continued on next page.)

OTHER PUBLICATIONS

A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43 No. 2, 1978 p. 358.

Conversion of Methyl Ketones into Terminal Acetylenes and (E)–Tri–substituted Olefins of Terpenoid Origin by Ei–ichi, Anthony O. King and William L. Klima, *J. Org. Chem.* 45 No. 12, 1980 p. 2526.

Sporn et. al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 1980 pp. 627–630.

Shudo et al. in *Chem. Phar. Bull.* 33:404–407 (1985).

(List continued on next page.)

*Primary Examiner*—Amelia Owens
*Attorney, Agent, or Firm*—Gabor L. Szekeres; Robert J. Baran; Martin A. Voet

[57] ABSTRACT

Compounds of Formula 1

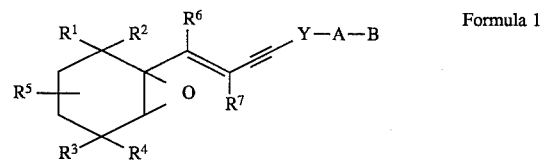

where $R_1$–$R_7$ are hydrogen, lower alkyl of 1–6 carbons, or halogen;

Y is phenyl, pyridyl, furyl, thienyl, pyridazinyl, pyrimidinyl, pyrazinyl, thiazolyl or oxazolyl;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_{14}$, $CR_{14}(OR_{12})_2$, or $CR_{14}OR_{13}O$, where $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, $R_{13}$ is divalent alkyl radical of 2–5 carbons and $R_{14}$ is an alkyl, cycloalkyl or alkenyl group containing 1 to 5 carbons, have retinoid-like biological activity.

36 Claims, No Drawings

U.S. PATENT DOCUMENTS

| | | | |
|---|---|---|---|
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1993 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,426,118 | 6/1995 | Chandraratna | 514/337 |

FOREIGN PATENT DOCUMENTS

| | | | |
|---|---|---|---|
| 3316932 | 11/1983 | Germany | C07C 63/66 |
| 3524199 | 1/1986 | Germany | C07C 63/66 |
| 3602473 | 7/1987 | Germany | C07C 43/215 |
| 3708060 | 9/1987 | Germany | C07D 311/04 |
| 3715955 | 11/1987 | Germany | C07C 15/58 |
| 2190378 | 11/1987 | United Kingdom | C07C 39/21 |
| 8500806 | 2/1985 | WIPO | A61K 31/00 |
| 8504652 | 10/1985 | WIPO | A61K 31/19 |
| WO9116051 | 10/1991 | WIPO | A61K 31/44 |
| WO9206948 | 4/1992 | WIPO | C07C 69/86 |
| 9321446 | 10/1993 | WIPO | C07C 69/76 |

OTHER PUBLICATIONS

Kagechika et. al. in *J. Med. Chem.* 31:2182–2192 (1988).

Chemistry and Biology of Synthetic Retinoids by Marcia I. Dawson and William H. Okamura, published by CRC Press Inc., 1990, pp. 334–335, 354.

Synthesis of 2,2'-Diacyl-1,1'-biaryls. Regiocontrolled Protection of . . . by Mervic, et al, *J. Org. Chem.*, No. 45, pp. 4720–4725, 1980.

A Dopamine Receptor Model and Its Application in the Design of a New Class of Rigid Pyrrolo[2,3-g]isoquinoline Antipsychotics, Gary L. Olson, et al. *American Chemical Society*, 1981, vo. 24, No. 9, pp. 1026–1031.

6.2.3 Conformational Restriction, Williams, et al., *Drug Discovery and Development*, 1987 The Humana Press, pp. 54–55.

V. Retinoid Structure–Biological Activity Relationships, Chemistry and Biology of Synthetic Retinoids, pp. 324–356, 1990.

Davis et al. *J. Organomettalic Chem* 387 (1990) 381–390.

Effects of 13-Cis-Retinoic Acid, All-Trans-Retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792–797.

Organ maintenance of human sebaceous glands: in vitro effects of 13-cis retinoic acid and testosterone, John Ridden, et al., *Journal of Cell Science*, vo. 95, 1990, pp. 125–136.

Characterization of Human Sebaceous Cells In Vitro, Thomas I. Doran, et al., *The Journal of Investigative Dermatology*, vol. 96, No. 3, Mar. 1991.

Synthesis and Evaluation of Stilbene and Dihydrostilbene Derivatives as Potential Anticancer Agents That Inhibit Tubulin Polymerization by Cushman, Mark et. al. *J. Med. Chem* 1991, 34, 2579–2588.

Synthesis and Evaluation of New Protein–Tyrosine Kinase Inhibitors. Part 1. Pyridine–Containing Stilbenes and Amides by Cushman, Mark et al. *Bioorganic & Medicinal Chemistry Letters*, vol. 1, No. 4, pp. 211–214, 1991.

Di–and Tri–methoxystyryl Derivatives of Heterocyclic Nitrogen Compounds by Bahner, C.T. et al. Arzneim–Forsch./Drug Res, 31 (I), Nr. 3 (1981).

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry*, 1989, 32, pp. 1098–1108.

[4-(1,2-EPOXYCYCLOHEXANYL)BUT-3-EN-1-YNYL]AROMATIC AND HETEROAROMATIC ACIDS AND DERIVATIVES HAVING RETINOID-LIKE BIOLOGICAL ACTIVITY

CROSS-REFERENCE TO RELATED APPLICATION

The present application is a divisional of application Ser. No. 08/177,620, filed on Dec. 30, 1993, to be issued as U.S. Pat. No. 5,426,118.

BACKGROUND OF THE INVENTION

FIELD OF THE INVENTION

The present invention is directed to novel compounds which have retinoid-like biological activity. More specifically, the present invention relates to but-3-en-1-ynyl compounds which are substituted in the 1-position by an aromatic or heteroaromatic acid or ester, and on the 4-position by an alkyl-substituted 1,2-epoxycyclohexanyl moiety. The aromatic acid function may also be converted to an alcohol, aldehyde or ketone, or derivatives thereof, or may be reduced to —$CH_3$.

RELATED ART

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis; eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

U.S. Pat. No. 4,739,098 describes but-3-en-1-ynyl compounds which are substituted in the 1-position by an aromatic acid or ester, and on the 4-position by an alkyl-substituted -1-cyclohexene moiety. U.S. Pat. No. 4,927,947 describes but-3-en-1-ynyl compounds which are substituted in the 1-position by a heteroaromatic acid or ester, and on the 4-position by an alkyl-substituted -1-cyclohexene moiety. The compounds described in these patents have retinoid-like biological activity.

SUMMARY OF INVENTION

The present invention relates to compounds of Formula 1

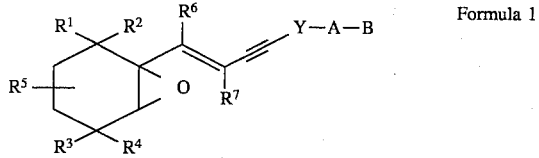

Formula 1 where $R_1$–$R_7$ are hydrogen, lower alkyl of 1–6 carbons, or halogen;

Y is phenyl, pyridyl, furyl, thienyl, pyridazinyl, pyrimidinyl, pyrazinyl, thiazolyl or oxazolyl;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_{14}$, $CR_{14}(OR_{12})_2$, or $CR_{14}OR_{13}O$, where $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, $R_{13}$ is divalent alkyl radical of 2–5 carbons and $R_{14}$ is an alkyl, cycloalkyl or alkenyl group containing 1 to 5 carbons.

In a second aspect, this invention relates to the use of the compounds of Formula 1 as regulators for cell proliferation and differentiation, and particularly as agents for treating dermatoses, such as ache, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing artherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damage to skin.

This invention also relates to a pharmaceutical composition comprising a compound of Formula 1 in admixture with a pharmaceutically acceptable excipient.

In another aspect, this invention relates to the process for making a compound of Formula 1, which process comprises reacting a compound of Formula 2, where the symbols $R_1$–$R_7$, Y, A and B are defined as in connection with Formula 1, with an epoxidizing agent; converting the ester of Formula 1 to an acid; and to prepare compounds in which A is $(CH_2)_n$ and n is 1–5, homologating a compound of Formula 1 to increase the value of n, or converting an acid of Formula 1 to an ester; or converting an acid of Formula 1 to an amide;

or reducing and acid of Formula 1 to an alcohol of aldehyde; or converting an alcohol of Formula 1 to an ether or ester; or converting an aldehyde of Formula 1 to an acetal.

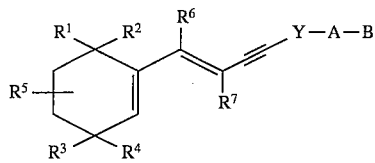

Formula 2

DETAILED DESCRIPTION OF THE INVENTION

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cyclo-alkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. It includes organic and inorganic esters. Where B (of Formula 1) is —COOH, this term covers the products derived from treatment of this function with alcohols or thioalcohols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is defined as above.

The term "amides" has the meaning classically accorded that term in organic chemistry. In this instance it includes the unsubstituted amides and all aliphatic and aromatic mono- and di- substituted amides.

A pharmaceutically acceptable salt may be prepared for any compounds in this invention having a functionality capable of forming such-salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

The compounds of the present invention contain at least one double bond and therefore may have trans and cis (E and Z) isomers, although trans (E) isomers of the but-3-ene double bond are preferred. In addition, the compounds of the present invention may contain two or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

The preferred compounds of this invention are those of Formula 1 where Y is phenyl, pyridyl, thienyl or furyl. When Y is phenyl, the preferred compounds are where the A–B group is para or meta to the but-3-ene-1-enyl chain on the benzene ring.

In the preferred compounds A is (CH$_2$)$_n$ and n is 0,1, or 2; and B is —COOH, an alkali metal salt or organic amine salt thereof. Alternatively, compounds are preferred where B is represented by COOR$_8$ (ester) where R$_8$ is lower alkyl, CONR$_9$R$_{10}$ where R$_9$ and R$_{10}$ are hydrogen or lower alkyl (amide) CH$_2$OH (alcohol), CH$_2$OCOR$_{11}$, CH$_2$OR$_{11}$ where R$_{11}$ is lower alkyl; (lower alkyl esters and ethers formed with lower alkanol). Generally speaking, the carboxylic acids esters and amides (B=COOH, COOR$_8$ or CONR$_9$R$_{10}$) are more preferred than the alcohol or its esters (B=CH$_2$OH or CH$_2$ $_{OCOR11}$)

With respect to the but-3-ene double bond, substituents about this bond are in the trans (E) configuration in the preferred compounds of this invention. The R$_6$ and R$_7$ substituents preferably are H, or lower alkyl, more preferably methyl or hydrogen. The R$_5$ substituent is preferably lower alkyl, most preferably methyl, and is preferably attached to the 2-position of the epoxidized cyclohexane ring. The R$_1$–R$_4$ substituents are preferably H or lower alkyl, and more preferably H or methyl.

Particularly preferred compounds of the invention are shown in Table 1 with reference to Formula 3 and Formula 4:

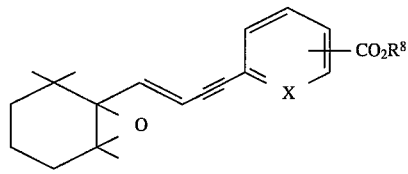

Formula 3

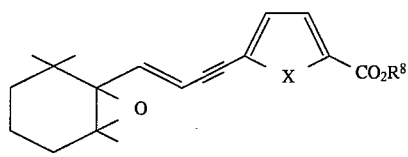

Formula 4

TABLE 1

| Compound No group | Formula | X | R$_8$ | position of COOR$_8$ |
|---|---|---|---|---|
| 1 | 3 | CH | H | 4 (para) |
| 2 | 3 | CH | H | (3) (meta) |
| 3 | 4 | S | H | n/a* |
| 4 | 3 | N | H | 5 |
| 5 | 3 | N | C$_2$H$_5$ | 5 |
| 6 | 4 | S | C$_2$H$_5$ | n/a* |
| 7 | 4 | O | H | n/a* |

*n/a = not applicable

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The retinoid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increases are unknown, it is known that 12-O-tetradecanoylphorbol-13-acetate (TPA) induces ODC activity. Retinoic acid inhibits this induction of ODC activity by TPA. An assay essentially following the procedure set out in Cancer Res: 1662–1670,1975 may be used to demonstrate inhibition of TPA induction of ODC by compounds of this invention. The results of this assay for certain examplary compounds of the invention are shown in Table 2 below.

TABLE 2

| Compound # | IC$_{80}$ (nmol) |
|---|---|
| 1 | 4.8 |
| 3 | 22.3 |
| 4 | 21 |
| 5 | 1.07 |
| 6 | 16 |

Synthetic Processes for Preparing Compounds of the Invention

The compounds of this invention can be made by the synthetic chemical pathways illustrated here. The synthetic chemist will readily appreciate that the conditions set out here are specific embodiments which can be generalized to any and all of the compounds represented by Formula 1.

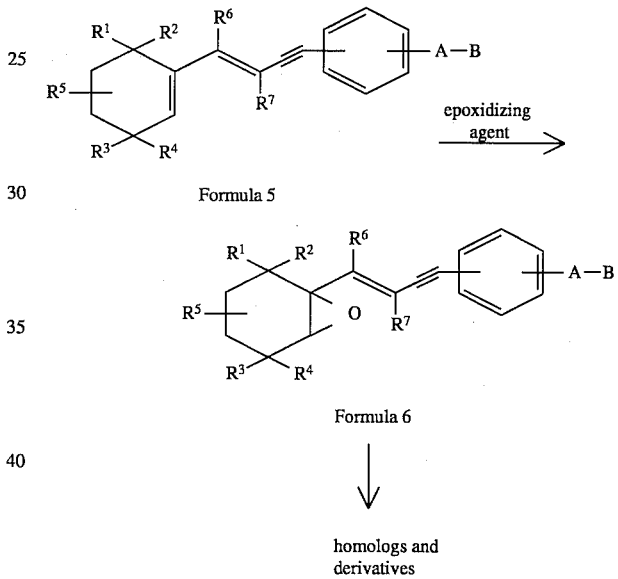

Reaction Scheme 1

In accordance with Reaction Scheme 1 a [4-(1-cyclohexenyl)but-3-ene-1-ynyl]phenyl derivative of Formula 5, which has the desired $R_1$–$R_7$ substituents (as defined in connection with Formula 1) and the A–B group (as defined in connection with Formula 1) attached to the phenyl group, is reacted with an epoxidizing agent to yield the epoxide compound of Formula 6. The starting compound of Formula 5 can be obtained in accordance with the disclosure of U.S. Pat. No. 4,739,098 which is expressly incorporated herein by reference. Generally speaking, the reaction of epoxidation is conducted in a secondary alcohol or ether type solvent such as iso-propyl alcohol or diethyl ether, under a protective blanket of inert gas, such as argon, at ambient temperature. Meta-chloroperoxybenzoic acid (MCPB) and magnesium monoperoxyphthalate (MMPP) serve as examples of preferred epoxidizing agents. The compounds of Formula 6, shown in Reaction Scheme 1, may already be the desired target compounds or may be readily converted into desired target compounds. This is indicated in Reaction Scheme 1 by conversion into "homologs and derivatives", by such steps as salt formation, esterification, desterification, amide formation and the like. These steps relating to chemical transformations of the A–B group, either before or after epoxide formation, as applicable, are further discussed below.

Carboxylic acids are typically esterified by refluxing the acid in a solution of the appropriate alcohol in the presence of an acid catalyst such as sulfuric acid or thionyl chloride. Alternatively, the carboxylic acid can be condensed with the appropriate alcohol in the presence of dicyclohexylcarbodiimide and N,N-dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

A means for making compounds where A is $(CH_2)_n$ (n is 1–5) is to subject the compounds of Formula 1, (or of Formula 6) where B is an acid or other function, to homologation, using the well known Arndt-Eistert method of homologation, or other known homologation procedures.

Compounds of Formula 1, where A is an alkenyl group having one or more double bonds can be made for example, by having the requisite number of double bonds incorporated into the halogenated aryl or heteroaryl intermediate which is reacted with an ethyne compound in the preparation of the compounds of Formula 5, within the teachings of U.S. pat. No. 4,739,098. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-carboxylic acid, ester or like carboxaldehyde. Compounds of Formula where the 1 A group has a triple (acetylenic) bond can be made by using the corresponding aryl or heteroaryl aldehyde intermediate. Such intermediate can be obtained by reactions well known in the art, for example, by reaction of a corresponding methyl ketone with strong base, such as lithium diisopropylamide.

The acids and salts derived from compounds of Formula 1 and of Formula 6 are readily obtainable from the corresponding esters. Basic saponification with an alkali metal base will provide the acid. For example, an ester of Formula 1 or of Formula 6 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

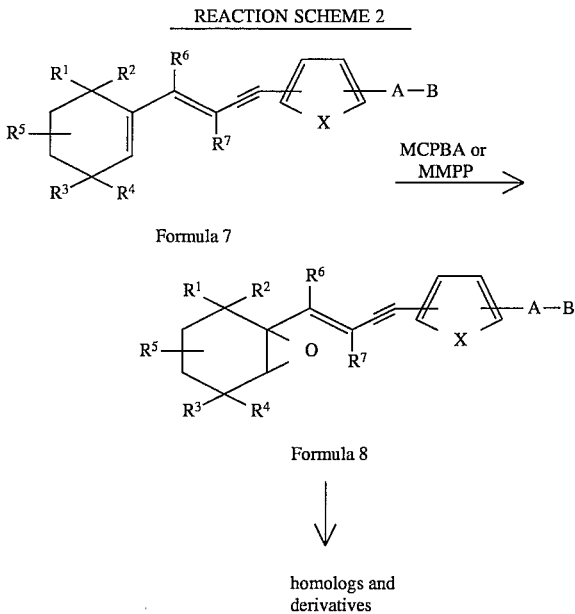

Formula 7

Formula 8 homologs and derivatives

Reaction Scheme 2 illustrates the synthesis of compounds of the invention where, with reference to Formula 1 the Y group is a 5-membered heterocyclic ring, such as thienyl or furyl. The starting material, a compound of Formula 7, is obtained in accordance with the teachings of U.S. Pat. No. 4,927,947, the specification of which is expressly incorporated herein by reference. The compounds of Formula 7 are reacted with an epoxidizing agent, such as metachloroperoxybenzoic acid magnesium monoperoxyphthalate, to yield the compounds of Formula 8. The compounds of Formula 8 may be the desired target compounds, or may be converted into desired target compounds by the transformations discussed in connection with Reaction Scheme 1.

REACTION SCHEME 3

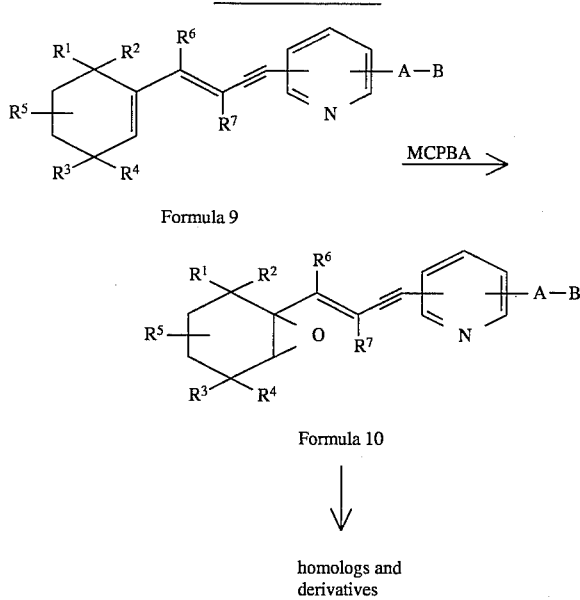

↓ homologs and
derivatives

Reaction Scheme 3 illustrates the synthesis of compounds of the invention where, with reference to Formula 1 the Y group is a 6-membered heterocyclic ring, such as pyridyl. The starting compounds of Formula 9 for this reaction scheme can also be obtained in accordance with the teachings of U.S. Pat. No. 4,927,947. The compounds of Formula 9 are epoxidized by reaction with meta-chloroperoxybenzoic acid or magnesium monoperoxyphthalate, to yield the compounds of Formula 10. The compounds of Formula 10 may be the desired target compounds, or may be converted into desired target compounds by the transformations discussed in connection with Reaction Scheme 1. This is indicated on the reaction scheme by conversion of compounds of Formula 10 into "homologs and derivatives".

Examples of reagents to be used within the teachings of U.S. Pat. Nos. 4,739,098 and 4,927,947 to obtain starting materials corresponding to compounds of Formula 2, Formula 5, Formula 7 and Formula 9, as applicable, are as follows:

ethyl 4-iodobenzoate;
ethyl 3-iodobenzoate;
ethyl 6-chloronicotinate;
ethyl 5-bromo-2-furoate;
ethyl 5-bromo-3-furoate;
ethyl 5-bromo-2-thiophenecarboxylate;
ethyl 5-bromo-3-thiophenecarboxylate;
ethyl 2-bromo-5-pyrazinecarboxylate;
ethyl 2-bromo-6-pyrazinecarboxylate;
ethyl 2-bromo-5-pyrimidinecarboxylate;
ethyl 2-bromo-6-pyrimidinecarboxylate;
ethyl 3-bromo-4-pyridazinecarboxylate;
ethyl 3-bromo-5-pyridazinecarboxylate;
1-(2',6',6'-trimethylcyclohex-1'-enyl)but-1-ene-3-yne;
1-(6',6'-dimethylcyclohex-1'-enyl)but-1-ene-3-yne;
1-(3',3',6',6'-tetramethylcyclohex-1'-enyl)but-1-ene-3-yne;
1-(2',3',3',6',6'-pentamethylcyclohex-1'-enyl)but-1-ene-3-yne.

Examples of compounds of Formula 2, Formula 5, Formula 7 and Formula 9, as applicable, which can be obtained from the above-noted reagents and are used in the epoxidation reactions disclosed in accordance with the present invention to obtain compounds of Formula 1, Formula 6, Formula 8 and Formula 10 are as follows:

ethyl 4-[4'-(2",6",6"-trimethylcyclohex-1-enyl)but-3'-en-1'-ynyl]benzoate;
ethyl 3-[4'-(2",6",6"-trimethylcyclohex-1-enyl)but-3'-en-1'-ynyl]benzoate;
ethyl 6-[4'-(2",6",6"-trimethylcyclohex-1-enyl)but-3'-en-1'-ynyl]nicotinate;
ethyl 5-[4'-(2",6",6"-trimethylcyclohex-1-enyl)but-3'-en-1'-ynyl]-2-furoate;
5-[4'-(2",6",6"-trimethylcyclohex-1-enyl)but-3'-en-1'-ynyl]thiophene-2-carboxylate;
ethyl 2-[4'-(2",6",6"-trimethylcyclohex-1-enyl)but-3'-en-1'-ynyl]pyrazine-5-carboxylate;
ethyl 2-[4'-(2",6",6"-trimethylcyclohex-1-enyl)but-3'-en-1'-ynyl]pyrimidine-6-carboxylate;
ethyl 2-[4'-(2",6",6"-trimethylcyclohex-1-enyl)but-3'-en-1'-ynyl]pyrimidine-6'-carboxylate;
ethyl 3-[4'-(2",6",6"-trimethylcyclohex-1-enyl)but-3'-en-1'-ynyl]pyridazine-4-carboxylate;
ethyl 3-[4'-(2",6",6"-trimethylcyclohex-1-enyl)but-3'-en-1'-ynyl]pyridazine-5-carboxylate;
ethyl 4-[4'-(6",6"-dimethylcyclohex-1-enyl)but-3'-en-1'-ynyl]benzoate;
ethyl 3-[4'-(6",6"-dimethylcyclohex-1-enyl)but-3'-en-1'-ynyl]benzoate;
ethyl 6-[4'-(6",6"-dimethylcyclohex-1-enyl)but-3'-en-1'-ynyl]nicotinate;
ethyl 5-[4'-(6",6"-dimethylcyclohex-1-enyl)but-3'-en-1'-ynyl]-2-furoate;
ethyl 5-[4'-(6",6"-dimethylcyclohex-1-enyl)but-3'-en-1'-ynyl]thiophene-2-carboxylate;
ethyl 2-[4'-(6",6"-dimethylcyclohex-1-enyl)but-3'-en-1'-ynyl]pyrazine-5-carboxylate;
ethyl 2-[4'-(6",6"-dimethylcyclohex-1-enyl)but-3'-en-1'-ynyl]pyrazine-6-carboxylate;
ethyl 2-[4'-(6",6"-dimethylcyclohex-1-enyl)but-3'-en-1'-ynyl]pyrimidine-5-carboxylate;
ethyl 2-[4'-(6",6"-dimethylcyclohex-1-enyl)but-3'-en-1'-ynyl]pyrimidine-6-carboxylate;
ethyl 3-[4'-(6",6"-dimethylcyclohex-1-enyl)but-3'-en-1'-ynyl]pyridazine-4-carboxylate;
ethyl 3-[4'-(6",6"-dimethylcyclohex-1-enyl)but-3'-en-1'-ynyl]pyridazine-5-carboxylate;
ethyl 4-[4'-(3",3",6",6"-tetramethylcyclohex-1-enyl)but-3'-en-1'-ynyl]benzoate;
ethyl 3-[4'-(3",3",6",6"-tetramethylcyclohex-1-enyl)but-3'-en-1'-ynyl]benzoate;
ethyl 6-[4'-(3",3",6",6"-tetramethylcyclohex-1-enyl)but-3'-en-1'-ynyl]nicotinate;
ethyl 5-[4'-(3",3",6",6"-tetramethylcyclohex-1-enyl)but-3'-en-1'-ynyl]-2-furoate;
ethyl 5-[4'-(3",3",6",6"-tetramethylcyclohex-1-enyl)but-3'-en-1'-ynyl]thiophene-2-carboxylate;
ethyl 2-[4'-(3",3",6",6"-tetramethylcyclohex-1-enyl)but-3'-en-1'-ynyl]pyrazine-5-carboxylate;
ethyl 2-[4'-(3",3",6",6"-tetramethylcyclohex-1-enyl)but-3'-en-1'-ynyl]pyrazine-6-carboxylate;
ethyl 2-[4'-(3",3",6",6"-tetramethylcyclohex-1-enyl)but-3'-en-1'-ynyl]pyrimidine-5-carboxylate;

ethyl 2-[4'-(3",3",6",6"-tetramethylcyclohex-1-enyl)but-3'-en-1'-ynyl]pyrimidine-6-carboxylate;

ethyl 3-[4'-(3",3",6",6"-tetramethylcyclohex-1-enyl)but-3'-en-1'-ynyl]pyridazine-4-carboxylate;

ethyl 3-[4'-(3",3",6",6"-tetramethylcyclohex-1-enyl)but-3'-en-1'-ynyl]pyridazine-5-carboxylate;

ethyl 4-[4'-(2",3",3",6",6"-pentamethylcyclohex-1-enyl)but-3'-en-1'-ynyl]benzoate;

ethyl 3-[4'-(2",3",3",6",6"-pentamethylcyclohex-1-enyl)but-3'-en-1'-ynyl]benzoate;

ethyl 6-[4'-(2",3",3",6",6"-pentamethylcyclohex-1-enyl)but-3'-en-1'-ynyl]nicotinate;

ethyl 5-[4'-(2",3",3",6",6"-pentamethylcyclohex-1-enyl)but-3'-en-1'-ynyl]-2-furoate;

ethyl 5-[4'-(2",3",3",6",6"-pentamethylcyclohex-1-enyl)but-3'-en-1'-ynyl]thiophene-2-carboxylate;

ethyl 2-[4'-(2",3",3",6",6"-pentamethylcyclohex-1-enyl)but-3'-en-1'-ynyl]pyrazine-5-carboxylate;

ethyl 2-[4'-(2",3",3",6",6"-pentamethylcyclohex-1-enyl)but-3'-en-1'-ynyl]pyrazine-6-carboxylate;

ethyl 2-[4'-(2",3",3",6",6"-pentamethylcyclohex-1-enyl)but-3'-en-1'-ynyl]pyrimidine-5-carboxylate;

ethyl 2-[4'-(2",3",3",6",6"-pentamethylcyclohex-1-enyl)but-3'-en-1'-ynyl]pyrimidine-6-carboxylate;

ethyl 3-[4'-(2",3",3",6",6"-pentamethylcyclohex-1-enyl)but-3'-en-1'-ynyl]pyridazine-4-carboxylate;

ethyl 3-[4'-(2",3",3",6",6"-pentamethylcyclohex-1-enyl)but-3'-en-1'-ynyl]pyridazine-5-carboxylate.

Examples of compounds of Formula 1, Formula 6, Formula 8 and Formula 10 (as applicable) other than the below described specific examples, which can be made in analogy to the below described specific examples, are:

ethy 4-[4'-(1",2"-epoxy -2",6",6"-trimethylcyclohexan-1-yl)but-3'-en-1'-ynyl]benzoate;

ethyl 3-[4'-(1",2"-epoxy-2",6",6"-trimethylcyclohexan-1-yl)but-3'-en-1'-ynyl]benzoate;

ethyl 5-[4'-(1",2"-epoxy-2",6",6"-trimethylcyclohexan-1-yl)but-3'-en-1'-ynyl]-2-furoate;

ethyl 2-[4'-(1",2"-epoxy-2",6",6"-trimethylcyclohexan-1-yl)but-3'-en-1'-ynyl]pyrazine-5-carboxylate;

ethyl 2-[4'-(1",2"-epoxy-2",6",6"-trimethylcyclohexan-1-yl)but-3'-en-1'-ynyl]pyrazine-6-carboxylate;

ethyl 2-[4'-(1",2"-epoxy-2",6",6"-trimethylcyclohexan-1-yl)but-3'-en-1'-ynyl]pyrimidine-5-carboxylate;

ethyl 2-[4'-(1",2"-epoxy-2",6",6"-trimethylcyclohexan-1-yl)but-3'-en-1'-ynyl]pyrimidine-6-carboxylate;

ethyl 3-[4'-(1",2"-epoxy-2",6",6"-trimethylcyclohexan-1-yl)but-3'-en-1'-ynyl]pyridazine-4-carboxylate;

ethyl 3-[4'-(1",2"-epoxy-2",6",6"-trimethylcyclohexan-1-yl)but-3'-en-1'-ynyl]pyridazine-5-carboxylate;

ethyl 4-[4'-(1",2"-epoxy-6",6"-dimethylcyclohexan- 1-yl)but-3'-en-1'-ynyl]benzoate;

ethyl 3-[4'-(1",2"-epoxy-6",6"-dimethylcyclohexan-1-yl)but-3'-en-1'-ynyl]benzoate;

ethyl 6-[4'-(1",2"-epoxy-6",6"-dimethylcyclohexan-1-yl)but-3'-en-1'-ynyl]nicotinate;

ethyl 5-[4'-(1",2"-epoxy-6",6"-dimethylcyclohexan-1-yl)but-3'-en-1'-ynyl]-2-furoate;

ethyl 5-[4'-(1",2"-epoxy-6",6"-dimethylcyclohexan-1-yl)but-3'-en-1'-ynyl]thiophene-2-carboxylate;

ethyl 2-[4'-(1",2"-epoxy-6",6"-dimethylcyclohexan-1-yl)but-3'-en-1'-ynyl]pyrazine-5-carboxylate;

ethyl 2-[4'-(1",2"-epoxy-6",6"-dimethylcyclohexan-1-yl)but-3'-en-1'-ynyl]pyrazine-6-carboxylate;

ethyl 2-[4'-(1",2"-epoxy-6",6"-dimethylcyclohexan-1-yl)but-3'-en-1'-ynyl]pyrimidine-5-carboxylate;

ethyl 2-[4'-(1",2"-epoxy-6",6"-dimethylcyclohexan-1-yl)but-3'-en-1'-ynyl]pyrimidine-6-carboxylate; ethyl 3-[4'-(1",2"-epoxy-6",6"-dimethylcyclohexan-1-yl)but-3'-en-1'-ynyl]pyridazine-4-carboxylate;

ethyl 3-[4'-(1",2"-epoxy-6",6"-dimethylcyclohexan-1-yl)but-3'-en-1'-ynyl]pyridazine-5-carboxylate;

ethyl 4-[4'-(1",2"-epoxy-3",3",6",6"-tetramethylcyclohexan-1-yl)but-3'-en-1'-ynyl]benzoate;

ethyl 3-[4'-(1",2"-epoxy-3",3",6",6"-tetramethylcyclohexan-1-yl)but-3'-en-1'-ynyl]benzoate;

ethyl 6-[4'-(1",2"-epoxy-3",3",6",6"-tetramethylcyclohexan-1-yl)but-3'-en-1'ynyl]nicotinate;

ethyl 5-[4'-(1",2"-epoxy-3",3",6",6"-tetramethylcyclohexan-1-yl)but-3'-en-1'-ynyl]-2furoate;

ethyl 5-[4'-(1",2"-epoxy-3",3",6",6"-tetramethylcyclohexan-1-yl)but-3'-en-1'-ynyl]thiophene-2-carboxylate;

ethyl 2-[4'-(1",2"-epoxy-3",3",6",6"-tetramethylcyclohexan-1-yl)but-3'-en-1'-ynyl]pyrazine-5-carboxylate;

ethyl 2-[4'-(1",2"-epoxy-3",3",6",6"-tetramethylcyclohexan-1-yl)but-3'-en-1'-ynyl]pyrazine-6-carboxylate;

ethyl 2-[4'-(1",2"-epoxy-3",3",6",6"-tetramethylcyclohexan-1-yl)but-3'-en-1'-ynyl]pyrimidine-5-carboxylate;

ethyl 2-[4'-(1",2"-epoxy-3",3",6",6"-tetramethylcyclohexan-1-yl)but-3'-en-1'-ynyl]pyrimidine-6-carboxylate;

ethyl 3-[4'-(1",2"-epoxy-3",3",6",6"-tetramethylcyclohexan-1-yl)but-3'-en-1'-ynyl]pyridazine-4-carboxylate;

ethyl 3-[4'-(1",2"-epoxy-3",3",6",6"-tetramethylcyclohexan-1-yl)but-3'-en-1'-ynyl]pyridazine-5-carboxylate;

ethyl 4-[4'-(1",2"-epoxy-2",3",3",6",6"-pentamethylcyclohexan-1-yl)but-3'-en-1'-ynyl]benzoate;

ethyl 3-[4'-(1",2"-epoxy-2",3",3",6",6"-pentamethylcyclohexan-1-yl)but-3'-en-1'-ynyl]benzoate;

ethyl 6-[4'-(1",2"-epoxy-2",3",3",6",6"-pentamethylcyclohexan-1-yl)but-3'-en-1'ynyl]nicotinate;

ethyl 5-[4'-(1",2"-epoxy-2",3",3",6",6"-pentamethylcyclohexan-1-yl)but-3'-en-1'-ynyl]-2-furoate;

ethyl 5-[4'-(1",2"-epoxy-2",3",3",6",6"-pentamethylcyclohexan-1-yl)but-3'-en-1'-ynyl]thiophene-2-carboxylate;

ethyl 2-[4'-(1",2"-epoxy-2",3",3",6",6"-pentamethylcyclohexan- 1-yl)but-3'-en-1'-ynyl]pyrazine-5-carboxylate;

ethyl 2-[4'-(1",2"-epoxy-2",3",3",6",6"-pentamethylcyclohexan-1-yl)but-3'-en-1'-ynyl]pyrazine-6-carboxylate;

ethyl 2-[4'-(1",2"-epoxy-2",3",3",6",6"-pentamethylcyclohexan-1-yl)but-3'-en-1'-ynyl]pyrimidine-5-carboxylate;

ethyl 2-[4'-(1",2"-epoxy-2",3",3",6",6"-pentamethylcyclohexan-1-yl)but-3'-en-1'-ynyl]pyrimidine-6-carboxylate;

ethyl 3-[4'-(1",2"-epoxy-2",3",3",6",6"-pentamethylcyclohexan-1-yl)but-3'-en-1'-ynyl]pyridazine-4-carboxylate;

ethyl 3-[4'-(1",2"-epoxy-2",3",3",6",6"-pentamethylcyclohexan-1-yl)but-3'-en-1'-ynyl]pyridazine-5-carboxylate.

SPECIFIC EXAMPLES (±)-4-[(3E)-4-(1,2-Epoxy-2,6,6-trimethylcyclo-hexan-yl)but-3-en-1-ynyl)]benzoic acid (Compound 1)

To a suspension of 0.034 g (0.055 mmol) of 80% magnesium monoperoxyphthalate (MMPP) and 1 mL isopropyl alcohol was added enough water to just dissolve the solid (5 drops). This solution was added to a solution of 0.029 g (0.10 mmol) of 4-[(3E)-4-(2,6,6-trimethyl-1-cyclohexenyl)but-3-en-ynyl)]benzoic acid in 1 mL iso-propyl alcohol and stirred at ambient temperature for 24 hours. The solution was treated with 2 mL of brine solution and extracted with 3×10 mL dichloromethane.

The organic extracts were combined and washed with 5 mL saturated aqueous NaCl and then dried ($MgSO_4$). The solvent was removed in-vacuo and the residue purified by flash chromatography ($SiO_2$, 75:25, hexane:ethyl acetate) to give the title compound as white solid.

PMR($CDCl_3$): δ0.98(3H, s), 1.08(1H, m), 1.14 (3H, s), 1.22(3H, s), 1.37–1.55(3H, m), 1.79 (1H, m), 1.90(1H, m), 5.95(1H, d, J=15.7 Hz), 6.53(1H, d, J=15.7 Hz), 7.54(2H, d, J=8.4 Hz), 8.07(2H, d, J=8.4 Hz), 11.3(1H, brs).

(±)-3-[(3E)-4-(1,2-Epoxy-2,6,6-trimethylcyclo-hexan-yl)but-3-en-1-ynyl)]benzoic acid (Compound 2)

To a suspension of 0.037 g (0.060 mmol) of 80% magnesium monoperoxyphthalate (MMPP) and 1 mL iso-propyl alcohol was added enough water to just dissolve the solid (about 5 drops). This solution was added to a solution of 0.029 g (0.10 mmol) of 3-[(3E)-4-2(2,6,6-trimethyl-1-cyclohexenyl)but-3-en-ynyl)]benzoic acid in 1 mL iso-propyl alcohol and stirred at ambient temperature for 24 hours. The solution was treated with 2 mL of brine solution and extracted with 3×10 mL dichloromethane.

The organic extracts were combined and washed with 5 mL saturated aqueous NaCl and then dried ($MgSO_4$). The solvent was removed in-vacuo and the residue purified by flash chromatography ($SiO_2$, 75:25, hexane:ethyl acetate) to give the title compound as a white solid.

PMR ($CDCl_3$): δ0.98(3H, s), 1.11(1H, m), 1.14(3H, s), 1.22(3H, s), 1.38–1.56(3H, m), 1.76(1H, m), 1.90(1H, m), 5.92(1H, d, J=15.7 Hz), 6.51(1H,d, J=15.7 Hz), 7.42(1H, d, J=7.9 Hz), 7.45(1H, d, J=7.8 Hz), 7.66(1H, d, J=7.8 Hz), 8.03(1H, d, J=7.9 Hz), ~7.60(1H, brs).

(±)-5-[(3E)-4-(1,2-Epoxy-2,6,6-trimethylcyclo-hexan-yl)but-3-en-1-ynyl)]-2-thiophenecarboxylic acid (Compound 3)

To a solution of 0.050 g (0. 145 mmol) of ethyl (±)-5-[(3E) -4-(1,2-epoxy-2,6,6-trimethylcyclohexanyl)but-3-en-1-ynyl)]-2-thiophenecarboxylate (Compound 6) and 2.32 mL of THF under argon was added 0.580 mL (0.290 mmol) of 0.5N LiOH. The resulting solution was stirred at 55° C. for 3 hours, cooled to room temperature and the THF removed in-vacuo. The aqueous residue was washed with 0.5 mL diethyl ether, the layers separated, and the aqueous layer treated with diethyl ether (5 mL). The 2-phase solution was stirred rapidly and carefully acidified with 0.290 mL of 1N aqueous HCl.

The ether layer was separated quickly and washed with 1 mL saturated aqueous NaCl and then dried ($MgSO_4$). The solvent was removed in-vacuo to give the title compound as a yellow solid.

PMR ($CDCl_3$): δ0.97(3H, s), 1.09(1H, m), 1.14(3H, s), 1.21(3H, s), 1.26(1H, m), 1.44(2H, m), 1.79(1H, m), 1.89(1H, m), 5.93(1H, d, J=15.8 Hz), 6.53(1H, d, J=15.8 Hz), 7.15(1H, d, J=3.9 Hz), 7.74(1H, J=3.9 Hz), 11.57 (1H, brs).

Ethyl (±)-6-[(3E)-4-(1,2-Epoxy-2,6,6-trimethylcy-clohexanyl)but-3-en-1-ynyl)nicotinate (Compound 5)

0.106 g (0.310 mmol) of 50% meta-chloroperoxybenzoic acid (MCPBA) was added to a solution of 0.1 g (0.310 mmol) of ethyl 5-[(3E)-4-(2,6,6-trimethyl-1-cyclohexenyl)but-3-en-1-ynyl)nicotinate (used as a mixture with 0.6 g (0.310 mmol) of ethyl 3-chloronicotinate), in 10 mL of anhydrous diethyl ether under argon was stirred at ambient temperature for 18 hours. The solution was treated with 10 mL of water and extracted with 3×50 mL ether.

The organic extracts were combined and washed with 25 mL saturated aqueous NaCl and then dried ($MgSO_4$). The solvent was removed in-vacuo and the residue purified by flash chromatography ($SiO_2$, 90:10, hexane:ethyl acetate) to give the title compound as a yellow solid.

PMR ($CDCl_3$): δ0.97(3H, s), 1.10(1H, m), 1.14(3H, s), 1.21(3H, s), 1.40–1.54(3H, m), 1.43(3H, t, J=7.2 Hz), 1.78(1H, m), 1.90(1H, m), 4.39(2H, q, J=7.2 Hz), 5.96(1H, d, J=15.7 Hz), 9.68(1H, d, J=15.7 Hz), 7.51(1H, d, J=7.3 Hz), 8.27(1H, d, J=2.1, 8.2 Hz), 9.18 (1H, d, J=2.8 Hz).

(±)-6-[(3E)-4-(1,2-Epoxy-2,6,6-trimethylcyclo-hexan-yl)but-3-en-1-ynyl)]nicotinic acid (Compound 4)

To a solution of 0.055 g (0.162 mmol) of ethyl (±)-6-[(3E)-4-(1,2-epoxy-2,6,6-trimethylcyclohexanyl)but-3-en-1-ynyl)nicotinate (Compound 5) and 2.6 mL of THF under argon was added 0.648 mL (0.324 mmol) of 0.5N LiOH. The resulting solution was stirred at 55° C. for 1 hour, cooled to room temperature and the THF removed in vacou. The aqueous residue was treated with dichloromethane (3 mL), the 2-phase solution stirred rapidly, and carefully acidified with 0.310 mL of 1N aqueous HCL.

The organic layer was separated quickly and washed with 1 mL saturated aqueous NaCl and then dried ($MgSO_4$). The solvent was removed in-vacuo and to give the title compound as a yellow solid.

PMR ($CDCl_3$): δ0.96(3H, s), 1.05(1H, m), 1.12(3H, s), 1.20(3H, s), 1.25(1H, m), 1.44(2H, m), 1.78(1H, m), 1.90(1H, m), 5.96(1H, d, J=15.8 Hz), 6.69(1H, d, J=15.8 Hz), 7.55(1H, d, J=8.3 Hz), 8.38(1H, dd, J=2.0, 8.3 Hz), 9.31(1H, d, J=1.2 Hz), 12.62(1H,brs).

Ethyl(±)-5-[(3E)-4-(1,2-Epoxy-2,6,6-trimethylcyclo-hexanyl)but-3-en-1-ynyl)]-2thiophenecarboxylate (Compound 6)

0.288 g (0.838 mmol) of 50% meta-chloroperoxybenzoic acid (MCPBA) was added to a solution of 0.250 g (0.761 mmol) of ethyl 5-[(3E)-4(2,6,6-trimethyl-1-cyclohexenyl)but-3-en-1-ynyl)]-2-thiophenecarboxylate in 25 mL of anhydrous diethyl ether under argon and stirred at ambient temperature for 18 hours. The solution was treated with 10 mL of water and extracted with 3×50 mL ether.

The organic extracts were combined and washed with 25 mL saturated aqueous NaCl and then dried (MgSO$_4$). The solvent was removed in-vacuo and the residue purified by flash chromatography (SiO$_2$, 95:5, hexane:ethyl acetate) to give the title compound as a yellow solid.

PMR (CDCl$_3$): δ0.96(3H, s), 1.05(1H, m), 1.13(3H, s), 1.20(3H, s), 1.37(3H, t, J=7.1 Hz), 1.32–1.55(3H, m), 1.78(1H, m), 1.91(1H, m), 4.34(2H, q, J=7.1 Hz), 5.92(1H, d, J=15.6 Hz), 6.51(1H, d, J=15.6 Hz), 7.12(1H, d, J=4.0 Hz), 7.65(1H, d, J=4.0 Hz).

(±)-5-[(3E)-4-(1,2-Epoxy-2,6,6-(trimethylcyclohexanyl)but-3-en-1-ynyl)]-2-furoic acid (Compound 7)

To a suspension of 0.141 g (0.228 mmol) of 80% magnesium monoperoxyphthalate (MMPP) and 2 mL iso-propyl alcohol was added enough water to just dissolve the solid (0.3 mL). This solution was added to a solution of 0.054 g (0.190 mmol) of 5-[(3E)-4-(2,6,6-trimethyl-1-cyclohexenyl)but-3-en-1-ynyl)]-2-furoic acid in 1 mL iso-propyl alcohol and stirred at ambient temperature for 48 hours. The solution was treated with 4 mL of brine and extracted with 3×20 mL ethyl acetate.

The organic extracts were combined and washed with 10 mL saturated aqueous NaCl and then dried (MgSO$_4$). The solvent was removed in-vacuo and the residue purified by flash chromatography (SiO$_2$, 50:50, hexane:ethyl acetate) to give the title compound as a yellow solid.

PMR (CDCl$_3$): δ0.94(3H,s), 1.08(1H, m), 1.11(3H, s), 1.17(3H, s), 1.35–1.50(3H, m), 1.73(1H, m), 1.89(1H, m), 5.89(1H, d, J=15.7 Hz), 6.57 (1H, d, J=15.7 Hz), 6.62(1H, d, J=3.6 Hz), 7.25(1H, d, J=3.6 Hz), 9.15 (1H, brs).

What is claimed is:

1. A compound of the formula

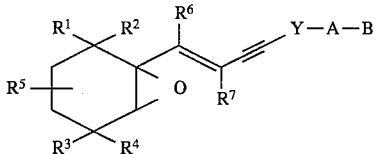

where $R_1$–$R_7$ are hydrogen, lower alkyl of 1–6 carbons, or halogen;

Y is phenyl, furyl and thienyl;

A is (CH$_2$)$_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_{14}$, CR$_{14}$(OR$_{11}$)$_2$, or CR$_{14}$OR$_{13}$O, where R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, R$_{13}$ is divalent alkyl radical of 2–5 carbons and R$_{14}$ is an alkyl, cycloalkyl or alkenyl group containing 1 to 5 carbons, or a pharmaceutically acceptable salt thereof.

2. A compound of claim 1 wherein A is (CH$_2$)$_n$ and n is 0.

3. A compound of claim 1 wherein B is COOH or a pharmaceutically acceptable salt thereof, or B is COOR$_8$.

4. A compound of claim 1 wherein R$_6$ and R$_7$ are hydrogen.

5. A compound of claim 1 where R$_1$ and R$_2$ are methyl.

6. A compound of claim 1 where R$_5$ is methyl.

7. A compound of claim 1 where R$_3$ and R$_4$ are hydrogen.

8. A compound of claim 1 where the configuration about the double bond in the but-3-ene-1-yne chain is trans.

9. A pharmaceutical composition comprising a pharmaceutically acceptable excipient and one or more compounds set forth in claim 1 as the active ingredient.

10. A method for treating skin disorders in a mammal which method comprises administering alone or in conjunction with a pharmaceutically acceptable excipient a therapeutically effective amount of one or more compounds set forth in claim 1.

11. A compound of the formula

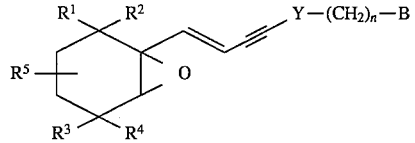

where $R_1$–$R_5$ are hydrogen or lower alkyl;

Y is phenyl, furyl, or thienyl;

n is 0–5; and

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_{14}$, CR$_{14}$(OR$_{12}$)$_2$, or CR$_{14}$OR$_{13}$O, where R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, R$_{13}$ is divalent alkyl radical of 2–5 carbons and R$_{14}$ is an alkyl, cycloalkyl or alkenyl group containing 1 to 5 carbons, or a pharmaceutically acceptable salt thereof.

12. A compound of claim 11 where Y is phenyl.

13. A compound of claim 12 where R$_3$ and R$_4$ are hydrogen.

14. A compound of claim of claim 13 where R$_5$ is methyl, and is attached to the 2 position of the cyclohexane ring.

15. A compound of claim 14 where n is 0.

16. A compound of claim 15 where B is COOH, a pharmaceutically acceptable salt thereof, COOR$_8$ or CONR$_9$R$_{10}$.

17. A compound of claim 16 where the configuration about the double bond in the but-3-ene-1-yne chain is trans.

18. A compound of claim 17 where B is COOH, a pharmaceutically acceptable salt thereof, or COOC$_2$H$_5$.

19. A compound of claim 18 where the B group is attached to the 4 position of the phenyl ring.

20. A compound of claim 18 where the B group is attached to the 3 position of the phenyl ring.

21. A compound of claim 11 where Y is thienyl.

22. A compound of claim 21 where R$_3$ and R$_4$ are hydrogen.

23. A compound of claim of claim 22 where R$_5$ is methyl, and is attached to the 2 position of the cyclohexane ring.

24. A compound of claim 23 where n is 0.

25. A compound of claim 24 where B is COOH, a pharmaceutically acceptable salt thereof, COOR$_8$ or CONR$_9$R$_{10}$.

26. A compound of claim 25 where the configuration about he double bond in the but-3-ene-1-yne chain is trans.

27. A compound of claim 26 where B is COOH, a pharmaceutically acceptable salt thereof, or COOC$_2$H$_5$.

28. A compound of claim 27 where the B group is attached to the 5 position of the thiophene ring.

29. A compound of claim 11 where Y is furyl.

30. A compound of claim 29 where R$_3$ and R$_4$ are hydrogen.

31. A compound of claim of claim 30 where R$_5$ is methyl, and is attached to the 2 position of the cyclohexane ring.

32. A compound of claim 31 where n is 0.

33. A compound of claim 31 where B is COOH, a pharmaceutically acceptable salt thereof, COOR$_8$ or CONR$_9$R$_{10}$.

34. A compound of claim 23 where the configuration about the double bond in the but-3-ene-1-yne chain is trans.

35. A compound of claim 34 where B is COOH, a pharmaceutically acceptable salt thereof, or COOC$_2$H$_5$.

36. A compound of claim 35 a where the B group is attached to the 5 position of the furan ring.

* * * * *

UNITED STATES PATENT AND TRADEMARK OFFICE
CERTIFICATE OF CORRECTION

PATENT NO. : 5,618,836　　　　　　　　　　　　PAGE 1 OF 2
DATED : April 8, 1997
INVENTOR(S) : Chandraratna et al.

It is certified that error appears in the above-indentified patent and that said Letters Patent is hereby corrected as shown below:

Column 4, line 24, "$CH_2OCOR_{11}$)" should be --$CH_2OCOR_{11}$)"--.
Column 7, line 35, after "Formula", add --1--.
Column 7, line 35, after "the", delete "1".
Column 10, line 13, before "5-[4'", add --ethyl--.
Column 10, line 19, "pyrimidine" should be --pyrazine--.
Column 10, line 19, after "carboxylate;", add as a new paragraph
--ethyl 2-[4'-(2'',6'',6''-trimethylcyclohex-1-enyl)-but-3'-en-1'-ynyl]pyrimidine-5-carboxylate;--.
Column 10, line 21, "-6'-" should be -- -6- --.
Column 12, line 16, after "hexan-1-yl)but-3'-en-1'", add -- - --.
Column 12, line 18, after "hexan-1-yl)but-3'-en-1'-ynyl]-2", add -- - --.
Column 12, line 44, after "clohexan-1-yl)but-3'-en-1'", add -- - -- - --.
Column 14, line 58, after "hexanyl)but-3-en-1-ynyl)]-2", add -- - --.
Column 14, line 63, after "5-[(3E)-4", add -- - --.
Column 18, line 2, "31" should be --32--.
Column 18, line 6, "23" should be --33--.
Column 18, line 11, after "35", delete "a".

UNITED STATES PATENT AND TRADEMARK OFFICE
CERTIFICATE OF CORRECTION

PATENT NO. : 5,618,836
DATED : April 8, 1997
INVENTOR(S) : Chandraratna et al.

It is certified that error appears in the above-indentified patent and that said Letters Patent is hereby corrected as shown below:

Column 3, line 1, "and" should be --an--.

Column 6, line 66, "desterification" should be --deesterification--.

Column 14, line 43, "in vacou" should be --in-vacuo--.

Column 14, line 46, "HCL" should be --HCl--.

Column 14, line 49, after "in-vacuo", delete "and".

Column 16, line 48, after "of", delete first occurence of "claim of".

Column 16, line 65, after "of", delete first occurence of "claim of".

Column 17, line 13, after "of", delete first occurence of "claim of".

Signed and Sealed this

Third Day of February, 1998

BRUCE LEHMAN

*Attest:*

*Attesting Officer*  *Commissioner of Patents and Trademarks*